Figure 1:
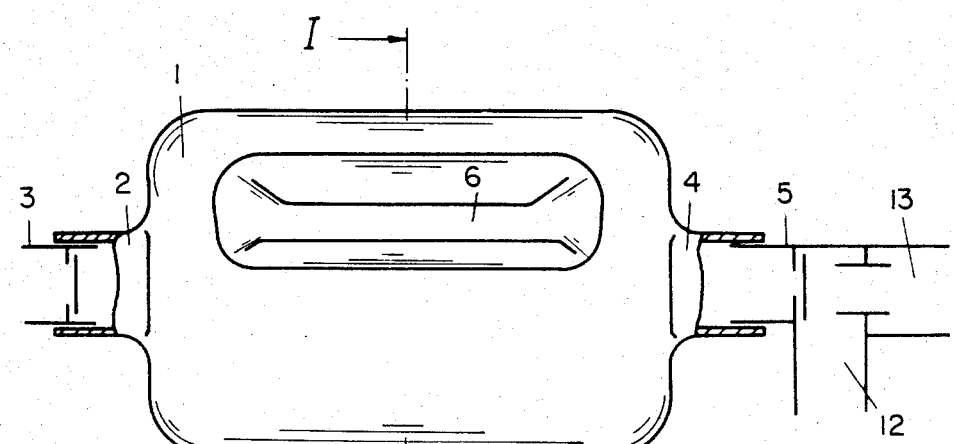

United States Patent [19]

Blumensaadt

[11] Patent Number: 4,537,191
[45] Date of Patent: Aug. 27, 1985

[54] PUMP ELEMENT OF A DEVICE FOR ARTIFICIAL RESPIRATION

[75] Inventor: Hans C. Blumensaadt, Virum, Denmark

[73] Assignee: Gottlieb Weinmann Geräte für Medizin und Arbeitsschutz G.m.b.H. & Co., Hamburg, Fed. Rep. of Germany

[21] Appl. No.: 505,910

[22] PCT Filed: Oct. 21, 1981

[86] PCT No.: PCT/EP81/00167
§ 371 Date: Jun. 20, 1983
§ 102(e) Date: Jun. 20, 1983

[87] PCT Pub. No.: WO83/01386
PCT Pub. Date: Apr. 28, 1983

[51] Int. Cl.³ .............................................. A61M 16/00
[52] U.S. Cl. ................................. 128/205.13; 604/212; D23/14; 222/210; 215/100 A; 220/94 A; 150/55
[58] Field of Search ............... 128/205.13, 205.16; 604/212, 216; D23/14; D24/23; D29/7, 8; 222/210, 214, 215, 206; 215/100 A; 220/94 A; 150/55

[56] References Cited

U.S. PATENT DOCUMENTS

| 3,063,620 | 11/1982 | Black | 92/90 |
| 3,356,100 | 12/1967 | Seeler | 128/205.13 |
| 4,077,404 | 3/1978 | Elam | 128/205.13 |
| 4,327,861 | 5/1982 | Thompson | 215/100 A |
| 4,405,321 | 9/1983 | Budoff | 604/212 |

FOREIGN PATENT DOCUMENTS 448923  12/1912  France ..................... 92/92

Primary Examiner—Henry J. Recla
Attorney, Agent, or Firm—Becker & Becker, Inc.

[57] ABSTRACT

A manually-operated pump element of a device for artificial respiration of human beings. The pump element includes a gas tight, elastomeric, self-expanding and preferably elongated hollow body, as well as two connecting pieces which respectively serve as an air-inlet and air-exit opening. Two indentations are integrated into the wall of the hollow body as grasping aids. With reference to the cross section of the hollow body, the indentations are separated from one another by an angle of 100° to 140°. In order to apply artificial respiration to a person, the hollow body is grasped with one hand at the indentations in such a way that the palm of the hand and the fingers span the periphery of the hollow body by approximately either 120° or 240°, as a result of which, when the hollow body is compressed with this hand, approximately one third or two thirds of the hollow body is emptied.

7 Claims, 4 Drawing Figures

PUMP ELEMENT OF A DEVICE FOR ARTIFICIAL RESPIRATION

The present invention relates to a manually-operated pump element of a device for artificial respiration of human beings, and comprises a gas tight, elastomeric, self-expanding and preferably elongated hollow body having an essentially circular cross section, and two connecting pieces therewith respectively as an air-inlet and an air-exit opening.

With known pump elements of this general type, the hollow body has a single or multiple wall, and has a valve element, operating as a suction valve, arranged in or on the connecting piece which serves as the air-inlet opening. On the other connecting piece, the air-exit opening, there is connected a line which leads to the person, the patient, to whom artificial respiration is to be applied; in this line a three-way valve, the patient valve, is inserted. During artifical respiration, air or gas is pressed out of the hollow body by manually compressing it, and this air or gas is pressed into the lungs of the patient via the air-exit opening and the line which contains the patient valve. In so doing, the suction valve in the air-inlet opening of the hollow body is closed. If the compressed hollow body is relieved, it again assumes its original shape due to its self-expanding properties, and fills via the suction valve with air from the atmosphere or with another gas that is supplied to the air-inlet opening from a storage tank. During this filling process, the patient valve prevents gas or air from flowing out of the lungs of the patient back into the hollow body, and at the same time provides a connection with the atmosphere, into which the exhaled air is withdrawn.

The use of such pump elements is connected with the danger that the patient is supplied with more air than the lungs of the patient receive during a single respiration due to which severe injuries can be inflicted to this person as a result of a pressure-overloading of the lungs. This danger is particularly great if the same pump element is to be used to apply artificial respiration to patients having greatly differing lung capacities, such as children and adults. This danger is prevented by equipping the pump elements with pressure limiters or relief devices in the form of relief pressure valves. However, such valves are not very reliable and easily become stopped up, as a result of which the pressure relief effect is lost. Another drawback of this pressure relief device is that the opening pressure is set too low. As a result, it is possible that the resistance in the air passages of the patient is not overcome, so that no artificial respiration is obtained.

Another possibility for protecting patients from injuries during artificial respiration and especially from injuries caused by the operation of the pump element, is to limit the quantity of air delivered during compression of the pump element. With the pump element described in U.S. Pat. No. 3,046,978-Lea dated July 3, 1962, this is accomplished by arranging two elastomeric spheres of different size in the hollow body at certain locations; these spheres limit the compression of the hollow body. Markings which delimit the grasping areas and which correspond to the position of the spheres are located on the outside of the hollow body. Each grasping area is thus associated with a specific volume of air, which corresponds approximately to the lung capacity of children, teenagers, and adults. These grasping areas can only be perceived optically, which, especially when applying artificial respiration to a person at a poorly illuminated site of an accident, can lead to incorrect operation of the pump element, and hence to injury to the patient. This drawback is magnified by the fact that the pump element is doublewalled, and that air is supposed to be blown into the space between its walls prior to use. This presupposes that the inner bag of the pump element is not compressed by air pressure in the intermediate space, which can only be achieved with relatively large self-expansion forces in the walls. However, these forces cause the pump element to be relatively difficult to operate, so that the user thereof cannot feel the artificial respiration pressure which is generated, which contributes to preventing a proper artificial respiration of the patient.

It is an object of the present invention to design a manually operated pump element of a device for artificial respiration of human beings in such a way that it can be used not only for treating children but also adults without the risk of a pressure-overloading of their lungs.

Starting from a pump element of the aforementioned general type, the object of the present invention is inventively realized in that two indentations which extend in the radial direction are integrated into the wall of the hollow body; these indentations, with reference to the cross section of the hollow body, are separated from one another by an angle of approximately 100° to 140°, and preferably appoximately 120°. Each of these indentations is expediently of such a size that the thumb or all of the tips of the other fingers of one hand can extend into them.

The operation of the pump element is conceivably simple, because the hollow body need only be grasped in such a way that the thumb and the tips of the other fingers of one hand respectively rest in one of the indentations. By clenching or opening the hand, the hollow body, in order to supply the patient with air, is pressed together and emptied, or, due to its self-expanding properties, is expanded and again filled with unused air. In this connection, the hollow body can be grasped in such a way that the palm of a hand and the fingers span either approximately 120° or 240° of the periphery of the body of the hollow body, as a result of which, when the hollow body is compressed, it is emptied either approximately one third or two thirds. The volume of the hollow body is measured in this connection in such a way that the smaller quantity of air delivered is adapted to the lung capacity of a child, and the larger quantity of air is adapted to the lung capacity of an adult. Since the two possibilities for grasping the hollow body are conspicuously different, and the fingers of the pumping hand are well guided in the indentations of the hollow body, it is possible to assure in the simplest manner without great technical expense that the lungs of a patient are not injured during artificial respiration.

To avoid possibly critical problems during artificial respiration, the self-expansion forces of the hollow body should be great enough that after compression at a speed which corresponds at least to the breathing frequency, the hollow body even unfolds or inflates if an operating error delays the unfolding. On the other hand, it is desirable to dimension the wall of the hollow body as thin as possible, in order to allow especially skilled personnel to feel the respiration or ventilation pressure generated by them when they compress the hollow body. In order to achieve this, it has been shown to be successful to integrate into the wall of the hollow body and to provide therewith recessed portions and/or beads which extend parallel to the indentations.

Figure 2:
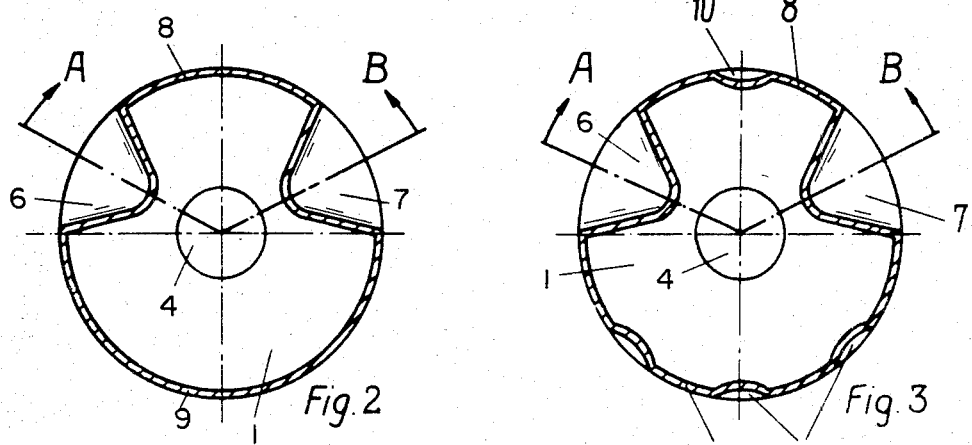
Figure 3:
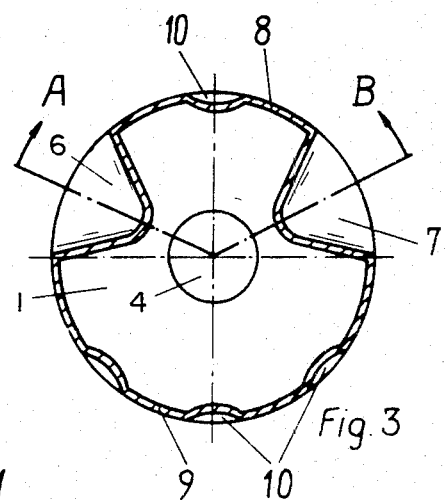
Figure 4:
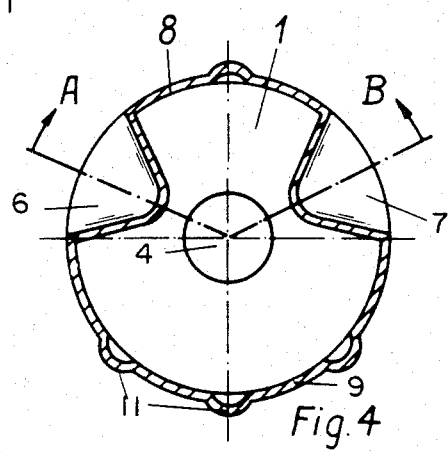

Exemplary embodiments of the present invention will be subsequently described with reference to the drawing, in which:

FIG. 1 is a schematic view of a device, for artificial respiration of human beings, having an inventive manually-operated pump element, FIG. 2 is a schematic sectional view taken along the line I—I through the pump element of FIG. 1, FIG. 3 is a view similar to that of FIG. 2 taken through another pump element, FIG. 4 is a view similar to that of FIG. 2 taken through a further pump element.

The device for artificial respiration of human beings shown in FIG. 1 has, as a pump element, an essentially cylindrical hollow body 1 made of a gas tight elastomeric material having self-expanding properties. Two connecting pieces 2, 4 as respective air-inlet and air-exit openings are joined to the hollow body 1. A suction valve 3 is connected to the connecting piece 2, while a patient valve 5 is connected to the connecting piece 4. Two axially extending indentations 6, 7 are integrated into the wall of the hollow body 1. With reference to the cross section of the hollow body 1, the indentations 6, 7 are separated from one another by an angle of approximately 120° (angle A-B, FIGS. 2, 3, and 4).

To improve the self-expanding properties of the hollow body 1, the wall thereof can be provided with recessed portions 10 (FIG. 3) and/or beads 11 (FIG. 4) which extend parallel to the indentations 6 and 7.

The operation and function of the illustrated pump element will be explained briefly as follows:

If the hollow body 1 is grasped with one hand in such a way that the palm of the hand extends over the portion 8 of the hollow body 1, and the thumb as well as the tips of the other fingers extend into the indentations 6 and 7 respectively, when the hand is clenched, a third of the air present in the hollow body 1 can be pressed out therefrom and into the lungs of the patient via the connecting piece 4 and the outlet 12 of the patient valve 5. In this connection, the suction valve 3 is closed, and the quantity of air delivered from the hollow body 1 is approximately 200 to 400 cm$^3$. This quantity of air is so small that there is no danger of damaging the lungs of a child during the application of artificial respiration. When the hand is opened, the hollow body 1 unfolds and is again filled with air by means of the suction valve 3. During this time, the patient exhales via the outlet 12 of the patient valve 5. This outlet 12 prevents the used air from flowing back into the hollow body 1. This used air is withdrawn to the atmosphere via the line 13.

If the palm of the hand which grasps the hollow body 1 extends over the portion 9 thereof, a quantity of air of approximately 800 to 1000 cm$^3$ is supplied to the patient via the patient valve 5 when the hand is clenched. This is the quantity of air which a grown person can receive during each respiration when artificial respiration is undertaken without danger to the lungs.

Pursuant to the present invention, the hollow body 1 which forms the pump element need not necessarily have the shape described in the figures, but can also, for example, be spherical or ellipsoid, as long as the indentations 6 and 7 are arranged in such a way that during operation of the hollow body in the manner described, either approximately one third or two thirds of the hollow body is emptied.

I claim:

1. A manually-operated pump element of a device for artificial respiration of human beings safely both as to children as well as adults having different lung capacity for volume of air to be supplied free of danger and without risk of pressure-overloading to lungs, respectively; said pump element comprising in combination:
   a gastight, elastomeric, self-expanding hollow body having a periphery and an essentially circular cross section; said hollow body including a wall having only two actual indentations integrated therein which extend in the axial direction of said hollow body; said two indentations, when viewed on a given cross section of said hollow body, being separated from one another by an angle in a range of approximately 100° to 140° as a result of which said hollow body can be grasped via the palm of the hand, and the fingers span the periphery of said hollow body by engagement therewith rather than visually so that when said hollow body is compressed manually, such hollow body thus being emptied either approximately one third or two thirds for children as well as adults respectively;
   a first tubular connecting piece joined to said hollow body as an air-inlet opening; and
   a second tubular connecting piece joined to said hollow body as an air-exit opening.

2. A pump element in combination according to claim 1, in which said two indentations are separated from one another by approximately 120°.

3. A pump element in combination according to claim 2, in which said gastight, elastomeric self-expanding hollow body is elongated.

4. A pump element in combination according to claim 3, in which each of said two indentations is of such a size that collectively the thumb and all of the tips of the fingers of one hand of a person operating said device respectively are receivable therein.

5. A pump element in combination according to claim 4, in which, integrated in said wall of said hollow body, there further are recessed portions which extend parallel to said two indentations.

6. A pump element in combination according to claim 5, in which, integrated in said wall of said hollow body, there further are beads which extend parallel to said two indentations.

7. A pump element in combination according to claim 6, in which, integrated in said wall of said hollow body, there are both recessed portions and also beads which extend parallel to said two indentations.

* * * * *